United States Patent [19]
Jarrett

[11] Patent Number: 6,117,428
[45] Date of Patent: *Sep. 12, 2000

[54] RUMINANT REPELLANT COMPOSITION AND METHOD FOR MAKING SAME

[76] Inventor: Rose Anne Jarrett, Green Rabbit Botanicals, LLC #9 Ninebark Lane, P.O. Box 162, Oxford, N.J. 07863

[*] Notice: This patent is subject to a terminal disclaimer.

[21] Appl. No.: 09/008,642

[22] Filed: Jan. 16, 1998

Related U.S. Application Data

[63] Continuation-in-part of application No. 08/786,273, Jan. 22, 1997, Pat. No. 5,738,851.

[51] Int. Cl.$^7$ .................................................. A61K 35/78
[52] U.S. Cl. ........................................................ 424/195.1
[58] Field of Search .......................................... 424/195.1

[56] References Cited

U.S. PATENT DOCUMENTS

| | | | |
|---|---|---|---|
| 4,965,070 | 10/1990 | Messina | 424/581 |
| 5,183,661 | 2/1993 | Messina | 424/405 |
| 5,368,866 | 11/1994 | Loucas | 424/581 |

OTHER PUBLICATIONS

Raver, Anne, At Long Last Daffodils (Now It Must Be Spring) The New Yorker.

Wang, S., et al., Headspace Sampling and Gas Chromatographic–mass Spectrometric Determination of Amphetamine and Methamphetamine in Betel, Journal of Chromatography A, 715 (1995) 325–331.

Vuorela, H., et al., Application of Headspace Gas Chromatography in Essential Oil Analysis. VII. Hydrodistillation Compared with Headspace, Progress in Essential Oil Research, 1986, pp. 551–554.

Loo, Albert et al., A Study on Narcissus Absolute Composition, Lawrence, B. M., et al., (Editors) Flavors and Fragrances: A World Perspective, Proceedings of the 10th International Congress of Essential Oils, Fragrances and Flavors, Washington, DC USA., Nov. 16–20, 1986, pp. 355–373.

Umano, Katsumi, et al., A New Method of Headspace Sampling: Grapefruit Volatiles, Lawrence, B. et al., (Editors) Flavors and Fragrances: A World Perspective, Proceedings of the 10th International Congress of Essential Oils, Fragrances and Flavors, Washington, DC, U.S.A., Nov. 16–20, 1986, pp. 981–998.

Frost, Pam, Scent Solutions, Scientists Explore New Ways to Make Flower–Friendly Perfumes and Colognes, Science World, Feb. 10, 1995.

Mookherjee, Braja, et al., Fruits and Flowers: Live vs. Dead—Which Do We Want? Lawrence, B. M., et al., (Editors), Flavors and Fragrances: A World Perspective, Proceedings of the 10th International Congress of Essential Oils, Fragrances and Flavors, Washington, DC, USA., Nov. 16–20, 1986, pp. 415–424.

Arnould, Cecile, et al. Sheep Food Repellents: Efficacy of Various Products, Habituation, and Social Facilitation, Journal and Chemical Ecology, vol. 19, No. 2, 1993, pp. 225–236.

*Primary Examiner*—Jean C. Witz
*Attorney, Agent, or Firm*—Richard P. Gilly

[57] ABSTRACT

Ruminant repellent compositions consisting essentially of active ingredients derived from, or equivalent to, chemicals found in plants in the Amaryllidaceae family. Particularly, ruminant repellent compositions consisting essentially of at least one of: Methods are also provided for protecting foliage from grazing by ruminants comprising applying a ruminant repellent composition of the present invention to the foliage, thereby imparting the taste and/or smell of certain plants in the Amaryllidaceae family to the vegetation, which is thus made unpalatable to browsing ruminants.

7 Claims, 3 Drawing Sheets

6,117,428

RUMINANT REPELLANT COMPOSITION AND METHOD FOR MAKING SAME

CROSS REFERENCE TO RELATED APPLICATION

This application is a continuation-in-part of application Ser. No. 08/786,273 filed Jan. 22, 1997, now issued as U.S. Pat. No. 5,738,851.

BACKGROUND OF THE INVENTION

1. Field of the Invention

The invention relates to all natural ruminant repellent compositions for discouraging ruminants from eating foliage. Specifically, the invention relates to compositions which are useful for deterring ruminants, particularly deer, from foraging on foliage upon which the compositions are applied. The invention further concerns methods for making the ruminant repellent compositions and methods for applying the same to various types of vegetation, e.g., flowers, plants, food crops, bushes and trees, that are subject to damage by browsing ruminants.

2. Background

Due to a lack of predators, the population of ruminants in rural and suburban neighborhoods has increased dramatically in recent years. In particular, deer populations in communities on the fringes of forested land increasingly forage on landscaped gardens, hedges, etc., resulting in costly and unsightly damage. Ruminants, including deer, also forage on saplings and agricultural crops, resulting in losses to timber producers and farmers, respectively.

Deer and certain other ruminants, however, are appealing animals. Accordingly it is unpopular to advocate the reduction of such ruminant populations by increased harvesting. Increased harvesting via hunting is also impractical or dangerous in suburban neighborhoods, where deer and other ruminant populations are increasing and the potential for foraging damage is acute.

It would be advantageous if these problems could be remedied short of extermination of the foraging ruminants, in particular to discourage the ruminants from foraging on ornamental plants and crops, and instead to revert to more natural food. The present invention provides a ruminant repellent composition that can be applied directly to vegetation to deter browsing by ruminants, namely by producing a taste and/or smell naturally associated with unpalatable plants. The compositions can be applied to various forms of vegetation without causing stress to the vegetation, and effectively discourage ruminant browsing for a period of time.

SUMMARY OF THE INVENTION

It is an aspect of the invention that plants susceptible to browsing damage by deer and other ruminants are protected from such browsing through the topical application of a ruminant repellent composition, particularly a ruminant repellent composition comprising chemicals that are either (a) contained in plants in the Amaryllidaceae family, or (b) equivalent to chemicals contained in plants in the Amaryllidaceae family.

Ruminant repellent compositions are provided which contain as active ingredients certain chemicals contained in, or equivalent to chemicals contained in, plants in the Amaryllidaceae family, namely

| | |
|---|---|
| *Narcissus* (common name Daffodil), | *Apodolirion,* |
| *Galanthus* (common name Snowdrops), | *Bomarea,* |
| Amaryllis Belladonna (common name Naked Lady), | *Boophone,* |
| Chlidanthus Fragrans, | *Brunsvigia,* |
| Crinium x Powellii (common name Crinium Lily), | *Calostemma,* |
| Cyrthanthus Elatus (common name Scarborough Lily) (also known as Vallota Purpurea), | *Carpolyza, Clivia,* |
| Scadoxus (*Haemanthus*) Multiflorus (common name Blood Lily), | *Cyanella,* |
| Sprekelia Formosissima (common name Jacobean Lily), | *Cybisetes,* |
| Leucojum (common name Snowflake), | *Eucrosia,* |
| Nerine Bowdenii, | *Eustephia,* |
| *Sternbergia* (common name Fall Daffodil), | *Gethyllis,* |
| Eucharis Amazonica (common name Amazon Lily), | *Griffinia,* |
| Hippeastrum (common name Amaryllis), | *Haemanthus,* |
| *Hymenocallis [; ](common name Peruvian Daffodil),* | *Urceclina,* |
| Zephyranthus (common name Fairy or Rain Lily), | *Ixiolirion,* |
| Pamianthe Peruviana, | *Lapiedra,* |
| Phaedranassa Carmioli Habranthus, | *Lepidochiton,* |
| *Lycoris,* | *Amarcrinum,* |
| *Pancratium,* | *Amarygia,* |
| *Paramongaia,* | *Ammocharis,* |
| *Phycella,* | *Plagiolirion,* |
| *Priophys,* | *Pyrolirion,* |
| *Rhodophiala,* | *Stenomesson,* |
| *Strumaria,* | *Ungernia,* |
| *Vagaria,* | *Worsleya,* and |
| Nerine Sarniensis; | | preferably
    Narcissus (common name Daffodil)
    Galanthus (common name Snowdrops);
most preferably
    Narcissus (common name Daffodil).

A method is provided for producing chemical compositions derived directly from plants in the Amaryllidaceae family that are useful as ruminant repellents. Specifically, a method is provided for producing ruminant repellent compositions from parts of certain plants in the Amaryllidaceae family, namely

| | |
|---|---|
| *Narcissus* (common name Daffodil), | *Apodolirion,* |
| *Galanthus* (common name Snowdrops), | *Bomarea,* |
| Amaryllis Belladonna (common name Naked Lady), | *Boophone,* |
| Chlidanthus Fragrans, | *Brunsvigia,* |
| Crinium x Powellii (common name Crinium Lily), | *Calostemma,* |
| Cyrthanthus Elatus (common name Scarborough Lily) (also known as Vallota Purpurea), | *Carpolyza, Clivia,* |
| Scadoxus (*Haemanthus*) | *Cyanella,* |
| Multiflorus (common name Blood Lily), | |
| Sprekelia Formosissima (common name Jacobean Lily), | *Cybisetes,* |
| Leucojum (common name Snowflake), | *Eucrosia,* |
| Nerine Bowdenii, | *Eustephia,* |
| *Sternbergia* (common name Fall Daffodil), | *Gethyllis,* |
| Eucharis Amazonica (common name Amazon Lily), | *Griffinia,* |
| Hippeastrum (common name Amaryllis), | *Haemanthus,* |
| Hymenocallis (common name Peruvian Daffodil), | *Urcelina,* |
| Zephyranthus (common name Fairy or Rain Lily), | *Ixiolirion,* |
| Pamianthe Peruviana, | *Lapiedra,* |
| Phaedranassa Carmioli Habranthus, | *Lepidochiton,* |
| *Lycoris,* | *Amarcrinum,* |
| *Pancratium,* | *Amarygia,* |
| *Paramongaia,* | *Ammocharis,* |
| *Phycella,* | *Plagiolirion,* |
| *Priophys,* | *Pyrolirion,* |
| *Rhodophiaia,* | *Stenomesson,* |
| *Strumaria,* | *Ungernia,* |
| *Vagaria,* | *Worsleya,* and |
| Nerine Sarniensis; | | preferably
    Narcissus (common name Daffodil)
    Galanthus (common name Snowdrops);

most preferably

Narcissus (common name Daffodil).

The method includes chopping or otherwise comminuting the plant parts, mixing the chopped product with a solvent, and filtering the resultant mixture to provide a filtrate solution. The ruminant repellent composition of the invention comprises the filtrate solution which contains the active ingredient or ingredients of the ruminant repellent.

A method is also provided for producing chemical compositions containing as active ingredients certain chemicals contained in, or equivalent to chemicals contained in, plants in the Amaryllidaceae family that are useful as ruminant repellents.

The method comprises combining a known organic or aqueous vehicle formulation suitable for transporting and administering ruminant repellent deterring agents to foliage and at least one of the above listed active ingredients.

The method for applying the ruminant repellent compositions of the instant invention to plants susceptible to browsing damage by deer and/or other ruminants, comprises direct application of the composition to the plants. Preferably, the concentrated ruminant repellent solution is diluted with a solvent, either aqueous or organic, and applied directly to the vegetation, leaves, flowers, stems and/or bark. The vegetation is thus rendered unpalatable to deer and/or other ruminants without causing stress to the vegetation.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

The following detailed description is of the best presently contemplated mode of carrying out the invention. The description is not intended in a limiting sense, and it is made solely for the purpose of illustrating the general principles of the invention. The various features and advantages of the present invention may be more readily understood with reference to the following detailed description taken in conjunction with the accompanying drawings.

Chemical compositions are provided which may be topically applied to plants to discourage browsing by deer and/or other ruminants by seeming to render the plants unpalatable. In particular, it is believed that the compositions alter the taste and/or smell characteristics of the plants to which they are applied, causing the deer and/or other ruminants to associate said plants with certain members of the Amaryllidaceae family, which ruminants are known not to browse on.

Figure 1:
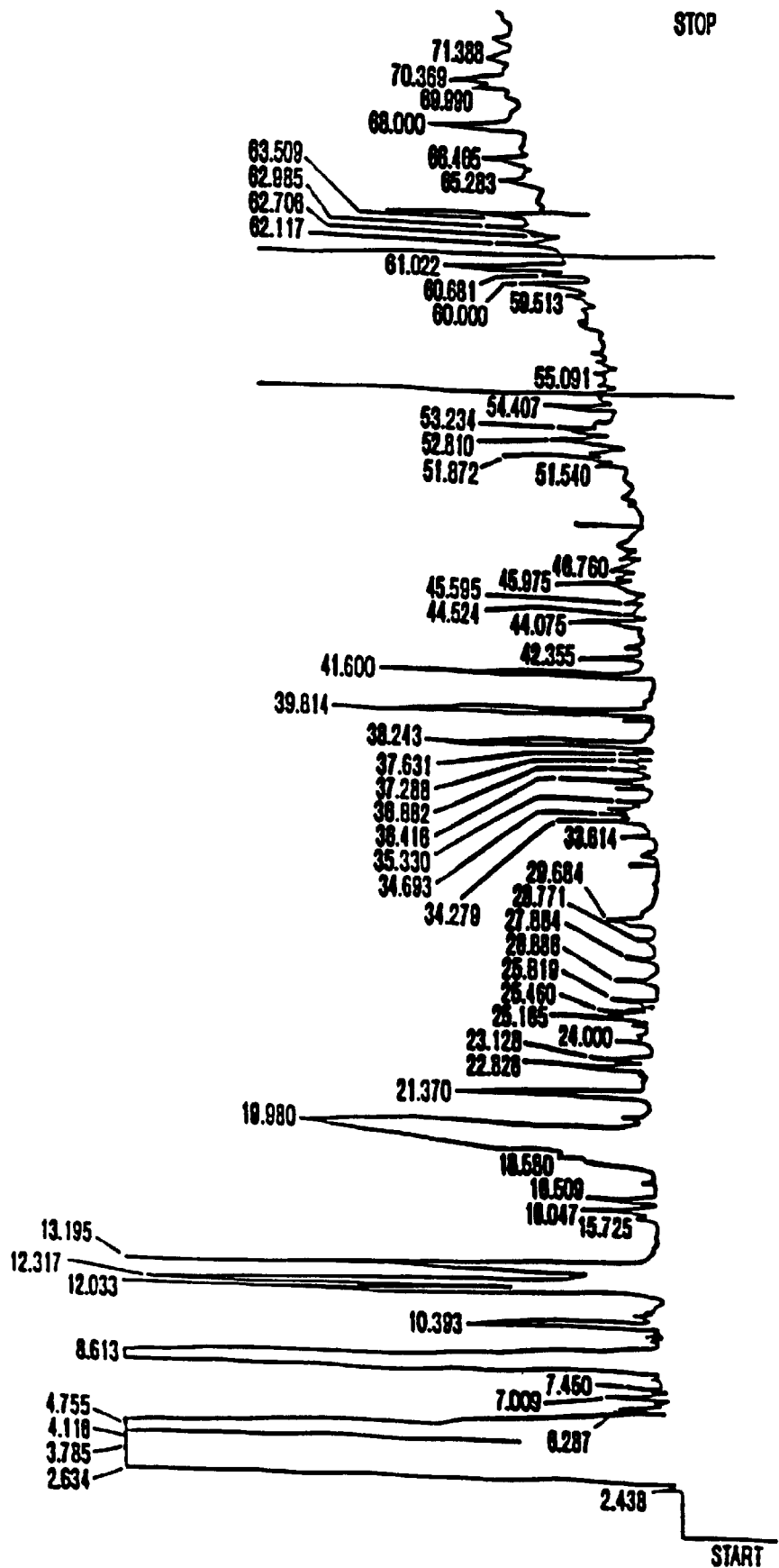
FIG. 1 is a depiction of the gas chromatographic output obtained for a sample of the ruminant repellent composition derived from Narcissus bulbs using a Hewlett-Packard HP-5890 Gas Chromatograph.

A vapor space extract of a ruminant repellent composition of the invention derived from Narcissus bulbs was captured in methylene chloride. It is believed that the vapor space extract contains the active ingredient or ingredients which give the ruminant repellent compositions of the present invention their ruminant repelling properties. The extract was analyzed using a Hewlett-Packard HP-5890 gas chromatograph and exhibits a characteristic Gas Chromatographic output substantially as shown in FIG. 1.

It is also believed that the ruminant repellent compositions of the present invention may be based on chemical compositions which contain chemicals which are identical, or equivalent, to the active ruminant repelling constituents found in plants in the Amaryllidaceae family.

It is believed that one or more of the above listed materials comprise the active constituents, or equivalents thereof, contained in plants in the Amaryllidaceae family, which impart to those plants their ruminant repellent properties.

An inventive method for preparing a ruminant repellent composition of the invention comprises a series of operations, generally as follows:

(a) comminuting parts of certain plants in the Amaryllidaceae family;

(b) mixing the comminuted plant material with a solvent; and, (c) filtering the resultant mixture to provide a solution containing active taste and smell agents, but substantially lacking plant solids.

Certain plants in the Amaryllidaceae family are known to be resistant to foraging by deer and other ruminants and are believed to contain an active ingredient or ingredients that give the ruminant repellent compositions of the invention their ruminant repellent properties. In particular, it is believed that the ruminant repellent compositions of the invention can be derived from any one of the following plants in the Amaryllidaceae family:

| | |
|---|---|
| *Narcissus* (common name Daffodil), | *Apodolirion,* |
| *Galanthus* (common name Snowdrops), | *Bomarea,* |
| Amaryllis Belladonna (common name Naked Lady), | *Boophone,* |
| Chlidanthus Fragrans, | *Brunsvigia,* |
| Crinium x Powellii (common name Crinium Lily), | *Calostemma,* |
| Cyrthanthus Elatus (common name Scarborough Lily) | *Carpolyza,* |
| (also known as Vallota Purpurea), | Clivia, |
| *Scadoxus (Haemanthus)* | *Cyanella,* |
| *Multiflorus* (common name Blood Lily), | |
| Sprekelia Formosissima (common name Jacobean Lily), | *Cybisetes,* |
| *Leucojum* (common name Snowflake), | *Eucrosia,* |
| Nerine Bowdenii, | *Eustephia,* |
| *Sternbergia* (common name Fall Daffodil), | *Gethyllis,* |
| Eucharis Amazonica (common name Amazon Lily), | *Griffinia,* |
| *Hippeastrum* (common name Amaryllis), | *Haemanthus,* |
| *Hymenocallis* (common name Peruvian Daffodil), | *Urceclina,* |
| *Zephyranthus* (common name Fairy or Rain Lily), | *Ixiolirion,* |
| Pamianthe Peruviana, | *Lapiedra,* |
| Phaedranassa Carnioli Habranthus, | *Lepidochiton,* |
| *Lycoris,* | *Amarcrinum,* |
| *Pancratium,* | *Amarygia,* |
| *Paramongaia,* | *Ammocharis,* |
| *Phycella,* | *Plagiolirion,* |
| *Priophys,* | *Pyrolirion,* |
| *Rhodophiala,* | *Stenomesson,* |
| *Strumaria,* | *Ungernia,* |
| *Vagaria,* | *Worsleya,* and |
| Nerine Sarniensis; | | preferably

Narcissus (common name Daffodil)

Galanthus (common name Snowdrops);

most preferably

Narcissus (common name Daffodil).

Regardless of the solvent used, the comminuted plant material is preferably mixed with the solvent by subjecting the constituents to vigorous agitation until they are thoroughly mixed. Preferably, the agitation is continued for a period of at least 1 minute. While the use of distilled water is disclosed as preferred, other solvents including organic solvents may be used provided the active ingredient or ingredients are soluble in said organic solvents and said organic solvents are non-toxic to the plants or crops to be treated with the repellent or the animals that might try to consume the treated plants and crops.

The filtrate may be diluted with additional solvent and sprayed directly onto vegetation to be protected from ruminant browsing using a pump spray bottle or other similar device. The extract may be reapplied as necessary to maintain the ruminant repellent effect.

The ruminant repellent compositions of the invention may preferably comprise chemical mixtures consisting essentially of at least one of the above listed materials.

Optionally, the ruminant repellant compositions of the invention may be incorporated into known formulations suitable for use as a vehicle for transporting and administering the active ingredients found in the ruminant repellant compositions of the present invention to vegetation through known means, e.g. via spraying.

One method for making the deer repellent composition of the invention may be further clarified by consideration of the following examples, which are intended to be exemplary and not limiting in nature.

The Narcissus (daffodil) bulbs used in the following examples were "Dutch Master" and "King Alfred" Trumpet Type Division I variety. Comminution and mixing was accomplished using a kitchen knife and an Osterizer Blender model Touch-A-Matic 14 Dual Range, manufactured by Hamilton Beach. Cheese cloth was used as the filter element for filtering the mixed plant solids and solvent. Cheese cloth is commercially available from Cadie Prod. Corp., Paterson, NJ under the designation Finest Quaiity Cheese Cloth.

EXAMPLE 1

About 82.5 g dormant daffodil bulbs were chopped with a knife and added to about 600 ml of distilled water. The combination was mixed in an Osterizer Blender on "High" using the "Grind" setting for about 1 minute, thereby further comminuting the plant solids as well as mixing the plant material with the water. The mixture was then filtered through 4 layers of cheese cloth. The filtrate solution was collected and transferred to a 1000 ml erlenmeyer flask. A 325 ml portion of the filtrate was poured into a spray bottle and applied to one section of a field of clover subject to browsing by deer. The field of clover was subsequently observed over a period of weeks. The treated clover was found to be significantly less foraged by deer than the neighboring control area of untreated clover.

Narcissus and Galanthus contain the alkaloid Lycorine, which is a known poison. Tests were done to demonstrate that the ruminant repellent compositions of the invention do not owe their effectiveness to lycorine. First, a vapor space extract of a ruminant repellent composition of the invention derived from Narcissus bulbs was captured in methylene chloride. The vapor space extract was analyzed using a Hewlett-Packard HP-5890 Series II gas chromatograph coupled with a HP-5971 Series mass selective detector operated in full scan mode. The results of that analysis demonstrated that the vapor space extract of the ruminant repellent composition did not contain lycorine.

Figure 2:
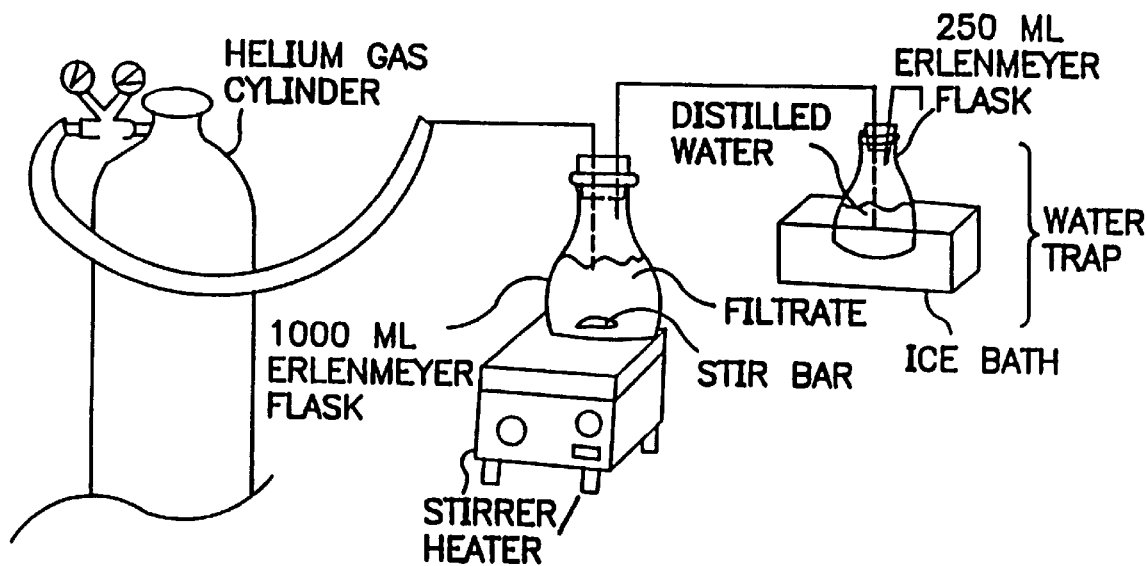
FIG. 2 is a depiction of a first apparatus for extracting active agents from the filtrate; and, FIG. 3 is a depiction of an alternative apparatus for extracting said active agents.
Figure 3:
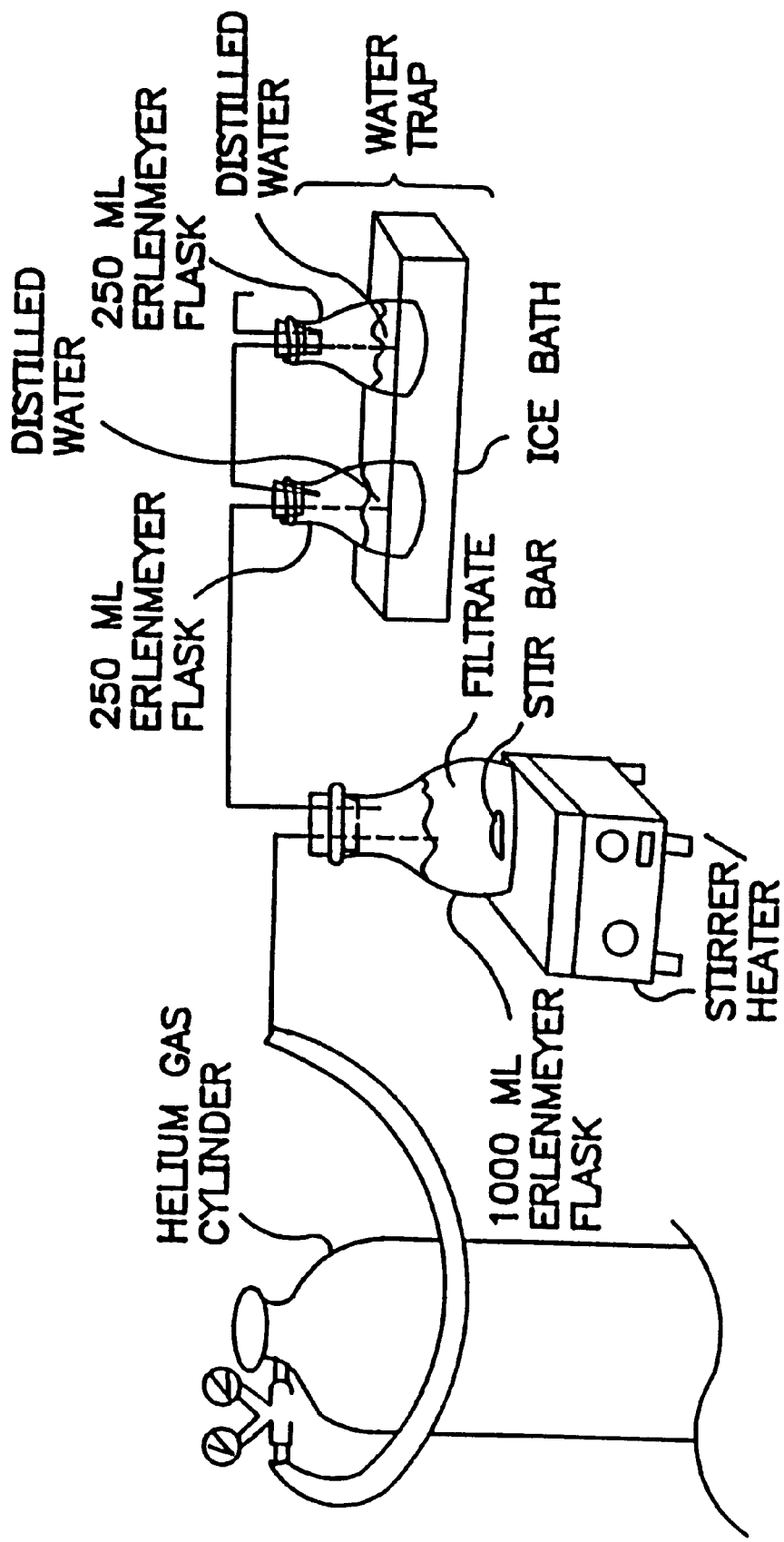

Second, vapor space extracts from the ruminant repellent compositions of the invention were obtained with an apparatus similar to that shown in FIG. 2 or FIG. 3 using the following procedure:

(a) sparging helium through the filtrate solution, while subjecting the filtrate solution to constant agitation and optionally with heat; and, (b) passing the sparged helium through a solvent trap maintained at about the freezing point temperature of water to extract the active agents of the product composition from the sparged helium.

These vapor space extracts were then applied to foliage to observe whether they exhibited ruminant repellent properties. The following examples describe the specific tests performed in greater detail.

EXAMPLE 2

About 82.5 g dormant daffodil bulbs were chopped with a knife and added to about 600 ml of distilled water. The combination was mixed in an Osterizer Blender on "High" using the "Grind" setting for about 1 minute, thereby further comminuting the plant solids as well as mixing the plant material with the water. The mixture was then filtered through 4 layers of cheese cloth. The filtrate solution was collected and transferred to a 1000 ml erlenmeyer flask. A 2" stir bar was added to the flask and the filtrate was subjected to agitation using a THERMOLYNE Type 1000 Series 463 stirrer/heat plate with the agitator speed dial set at ½ full speed (approximately 500 rpm). Helium gas was bubbled through the filtrate and into about 225 ml of distilled water contained in a 250 ml erlenmeyer flask located in an ice bath. The apparatus used is generally depicted in FIG. 2. The gas bubbling continued for about 3 hours. The active ingredient captured in the 225 ml water trap was diluted with an additional 100 ml of distilled water to provide 325 ml of repellent. The 325 ml was poured into a spray bottle and applied to one section of a field of clover subject to browsing by deer. The field of clover was subsequently observed over a period of weeks. The treated over was found to be less significantly foraged by deer than the neighboring control area of untreated clover.

EXAMPLE 3

The test used in Example 1 was repeated with similar results using an extract produced using the following process. Daffodil bulbs were chopped with a knife. bout 82.5 g of the chopped daffodil bulbs were added to about 600 ml of distilled water. The combination was mixed in an Osterizer Blender on "High" using the "Grind" setting for about 1 minute. The mixture was then filtered through 4 layers of cheese cloth. The filtrate was collected and transferred to a 1000 ml erlenmeyer flask. A 2" stir bar was added to the flask and the filtrate was subjected to agitation using a THERMOLYNE Type 1000 Series 463 stirrer/heat plate with the agitator dial set at ½ full speed and with the heater dial set at 1. Using the same apparatus used in Example 1, helium gas was bubbled through the filtrate into about 225 ml of distilled water contained in a 250 ml erlenmeyer flask located in an ice bath. The gas bubbling continued for about 6 hours. The active ingredient captured in the 225 ml water trap was diluted with an additional 100 ml of distilled water to provide about 325 ml of ruminant repellent.

EXAMPLE 4

The test used in Example 1 was repeated with more promising results using an extract produced using the following process. Daffodil bulbs were chopped with a knife. About 82.5 g of the chopped daffodil bulbs were added to about 600 ml of distilled water. The combination was mixed in an Osterizer Blender on "High" using the "Grind" setting for about 1 minute. The mixture was then filtered through 4 layers of cheese cloth. The filtrate was collected and transferred to a 1000 ml erlenmeyer flask. A 2" stir bar was added to the flask and the filtrate was subjected to agitation using a THERMOLYNE Type 1000 Series 463 stirrer/heat plate with the agitator dial set at ½ full speed and the heater dial set at 1. Helium gas was bubbled through the filtrate into about 225 ml of distilled water contained in a first 250 ml erlenmeyer flask located in an ice bath. The Helium, with any entrained gases, passing through the 225 ml water trap was bubbled through about 100 ml of distilled water contained in a second 250 ml erlenmeyer flask connected in series with the first and also located in an ice bath. The apparatus used is generally depicted in FIG. 3. The gas bubbling continued for about 12 hours. The contents of the two 250 ml erlenmeyer flasks were combined to provide about 325 ml of ruminant repellent.

EXAMPLE 5

About 170 g daffodil bulbs were chopped with a knife and were added to about 900 ml of distilled water. The combination was mixed in an Osterizer Blender on "High" using the "Grind" setting for about 1 minute. The mixture was then filtered through 4 layers of cheese cloth. The filtrate was collected and transferred to a 1000 ml erlenmeyer flask. A 2" stir bar was added to the flask and the filtrate was subjected to agitation using a THERMOLYNE Type 1000 Series 463 stirrer/heat plate with the agitator dial set at ½ full speed and with the heater dial set at 1. Helium gas was bubbled through the filtrate into about 1000 ml of distilled water contained in a 1000 ml erlenmeyer flask and then into 200 ml of distilled water in a 225 ml flask. Both the 1000 ml flask and the 225 ml flask were located in an ice bath. The gas bubbling continued for about 6 hours. The active ingredient captured in both the 1000 ml flask and the 225 ml flask was combined to provide 1200 ml of repellent.

Previous observations of the deer herd populating the vicinity of the test site demonstrated a proclivity for grazing on hosta plants. To test the effectiveness of the ruminant repellent compositions of the invention for repelling grazing deer four hosta plants, two untreated and two treated, were placed at the test site and observed. The treated plants were treated using the ruminant repellent composition of the invention as described above, namely by spraying the composition derived from the above process onto the hosta plant leaves and stalks. The site was surveyed on a daily basis. All four plants remained substantially untouched during the first three days. By the fourth day, while the plants treated with the ruminant repellent composition showed signs of only minor browsing or nibbling by deer, the untreated plants showed signs of significant foraging with about one-half to two-thirds of their leaves browsed off by deer.

While certain present preferred embodiments of the invention have been illustrated and described, it is to be understood that the invention is not limited thereto and may be otherwise practiced within the scope of the following claims.

I claim:

1. A method for protecting foliage from browsing by ruminants, comprising spraying on the foliage an effective amount of a ruminant repellant composition derived from plants selected from the group of Amaryllidaceae consisting of Narcissus (common name Daffodil), Amaryllis Belladonna (common name Naked Lady), Crinium x Powelli (common name Crinium Lily), Cyrthanthus Elatus (also known as Vallota Purpurea; common name Scarborough Lily), Scadoxus (Haemanthus) Multiflorus (common name Blood Lily), Sprekelia Formosissima (common name Jacobean Lily), Nerine Bowdenii, Nerine Sarniensis, Eucharis Amazonica (common name Amazon Lily), Zephyranthus (common name Fairy or Rain Lily), Galanthus (common name Snowdrops), Chlidanthus Fragrans, Leucojum (common name Snowflake), Sternbergia (common name Fall Daffodil), Hippeastrum (common name Amaryllis), Hymenocallis (common name Peruvian Daffodil), Pamianthe Peruviana, Phaedranassa Carmioli Habranthus, Amarcrinum, Amarygia, Ammocharis, Apodolirion, Bomarea, Boophone, Brunsvigia, Calostemma, Carpolyza, Clivia, Cyanella, Cybisetes, Eucrosia, Eustephia, Gethyllis, Griffinia, Haemanthus, Urceclina, Ixiolirion, Lapiedra, Lepidochiton, Lycoris, Pancratium, Paramongaia, Phycella, Plagiolirion, Priophys, Pyrolirion, Rhodophiala, Stenomesson, Strumaria, Ungernia, Vagaria, and Worsleya.

2. The method of claim 1, wherein ruminant repellent composition is prepared by:

(a) comminuting the plants;

(b) mixing the comminuted plants with a solvent;

(c) filtering the resultant mixture, and (d) collecting the filtrate.

3. The method of claim 1, wherein the ruminant repellent composition is produced by:

(a) comminuting Narcissus bulbs, (b) mixing the comminuted bulbs with a solvent, (c) filtering the resultant mixture, and (d) collecting the filtrate.

4. The ruminant repellent of claim 1, wherein the plants are Narcissus.

5. The ruminant repellent of claim 1, wherein the plants are Narcissus bulbs.

6. The ruminant repellent of claim 5, wherein the bulbs are selected from the group consisting of "Dutch Master" and "King Alfred" Trumpet Type Division I variety.

7. The ruminant repellent of claim 1, wherein the plants are Lycoris.

* * * * *